(12) United States Patent
Anastassiou et al.

(10) Patent No.: US 8,290,715 B2
(45) Date of Patent: *Oct. 16, 2012

(54) SYSTEM AND METHOD FOR MULTIPLE-FACTOR SELECTION

(75) Inventors: Dimitris Anastassiou, Tenafly, NJ (US); Vinay Varadan, Hastings-on-Hudson, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 334 days.

This patent is subject to a terminal disclaimer.

(21) Appl. No.: 12/133,045

(22) Filed: Jun. 4, 2008

(65) Prior Publication Data

US 2008/0300799 A1   Dec. 4, 2008

Related U.S. Application Data

(63) Continuation of application No. PCT/US2006/061749, filed on Dec. 7, 2006.

(60) Provisional application No. 60/748,662, filed on Dec. 7, 2005, provisional application No. 60/754,102, filed on Dec. 27, 2005.

(51) Int. Cl.
- *A61B 5/00* (2006.01)
- *G01N 33/48* (2006.01)
- *G01N 33/00* (2006.01)
- *G06F 19/00* (2011.01)

(52) U.S. Cl. ........... 702/20; 600/300; 702/189; 708/200

(58) Field of Classification Search .................. 209/1, 2; 600/300; 702/1, 19, 20, 32, 127, 179, 181, 702/187, 189; 708/100, 131, 160, 200, 422, 708/424

See application file for complete search history.

(56) References Cited

U.S. PATENT DOCUMENTS

| | | | | |
|---|---|---|---|---|
| 3,286,177 | A * | 11/1966 | Boer et al. | 324/103 R |
| 3,354,297 | A * | 11/1967 | Anderson et al. | 708/422 |
| 3,449,553 | A * | 6/1969 | Swan | 708/5 |
| 3,535,084 | A * | 10/1970 | Isawa et al. | 436/52 |
| 5,597,719 | A * | 1/1997 | Freed et al. | 435/194 |
| 5,715,821 | A * | 2/1998 | Faupel | 600/302 |
| 6,110,109 | A * | 8/2000 | Hu et al. | 600/300 |
| 6,996,476 | B2 | 2/2006 | Najarian | |

(Continued)

FOREIGN PATENT DOCUMENTS

WO   WO 2004/019264   3/2004

(Continued)

OTHER PUBLICATIONS

Bi et al., 2004, "Bipartite pattern discovery by entropy minimization-based multiple local alignment," *Nucleic Acids Research*, vol. 32, No. 17: p. 4979-4991.

(Continued)

*Primary Examiner* — Edward Cosimano

(57) ABSTRACT

The disclosed subject matter provides techniques for multiple-factor selection. The factors can be features or elements that are jointly associated with one or more outcomes by their joint presence or absence. There may be a non-causative correlation between the factors, features, or elements and the outcomes. In some embodiments, Entropy Minimization and Boolean Parsimony (EMBP) is used to identify modules of genes jointly associated with disease from gene expression data, and a logic function is provided to connect the combined expression levels in each gene module with the presence of disease. The smallest module of genes whose joint expression levels can predict the presence of disease can be identified.

22 Claims, 8 Drawing Sheets

U.S. PATENT DOCUMENTS

| | | | |
|---|---|---|---|
| 8,086,409 B2 * | 12/2011 | Anastassiou et al. | 702/19 |
| 2003/0104463 A1 | 6/2003 | Schuermann et al. | |
| 2003/0215866 A1 | 11/2003 | Liebovitch et al. | |
| 2004/0241730 A1 | 12/2004 | Yakhini et al. | |
| 2004/0253637 A1 * | 12/2004 | Buechler et al. | 435/7.1 |
| 2007/0178526 A1 * | 8/2007 | Kountakis et al. | 435/7.1 |
| 2007/0299645 A1 * | 12/2007 | Shapiro et al. | 703/11 |
| 2009/0012719 A1 * | 1/2009 | Anastassiou et al. | 702/20 |
| 2009/0299643 A1 * | 12/2009 | Anastassiou et al. | 702/19 |
| 2011/0144917 A1 * | 6/2011 | Anastassiou et al. | 702/19 |

FOREIGN PATENT DOCUMENTS

| | | | |
|---|---|---|---|
| WO | WO 2007/067956 A2 * | 6/2007 | |
| WO | WO 2007/134167 A2 * | 12/2007 | |

OTHER PUBLICATIONS

Hamer et al., 2003 "Rational Design of Drugs That Induce Human Immunodeficiency Virus Replication," *Journal of Virology*, vol. 77, No. 19: p. 10227-10236.

Furlanello et al., 2003, "Entropy-based gene ranking without selection bias for the predictive classification of microarray data," *BMC Bioinformatics*, 4:54.

Liu et al., 2005, "An Entropy-based gene selection method for cancer classification using microarray data," *BMC Bioinformatics*, 6:76.

U.S. Appl. No. 12/022,862, filed Jan. 30, 2008.
U.S. Appl. No. 12/307,694, filed May 4, 2009.
U.S. Appl. No. 13/013,321, filed Jan. 25, 2011.
U.S. Appl. No. 12/022,862, Feb. 20, 2008 Missing Parts.
U.S. Appl. No. 12/022,862, Sep. 22, 2008 Response to Missing Parts.
U.S. Appl. No. 12/022,862, Sep. 17, 2010 Restriction Requirement.
U.S. Appl. No. 12/022,862, Dec. 14, 2010 Response to Restriction Requirement.
U.S. Appl. No. 12/022,862, Feb. 18, 2011 Non-Final Office Action.
U.S. Appl. No. 12/307,694, Feb. 2, 2009 Petition under 37 CFR 1.137(b).
U.S. Appl. No. 12/307,694, Mar. 11, 2009 Missing Requirements.
U.S. Appl. No. 12/307,694, May 4, 2009 Response to Missing Requirements.
U.S. Appl. No. 13/013,321, Feb. 10, 2011 Notice to File Corrected Application Papers.
U.S. Appl. No. 13/013,321, Mar. 1, 2011 Response to Notice to File Corrected Application Papers.
Bassett et al., 1999, "Gene Expression Informatics—It's All in Your Mine", *Nature Genetics Supplement*, vol. 21, pp. 51-55.
Boser, B.E., Guyon, I.M. & Vapnik, V.N.; A training algorithm for optimal margin classifiers, in $5^{th}$ *Annual Workshop con COLT*, (ed. Haussler, D.) pp. 144-152, ACM Press 1992.
Brazma et al., 2000, "Gene Expression Data Analysis", *FEBS Lett.*, vol. 480, pp. 17-24.

Eisen, M.B., Spellman, P.T., Brown, P.O. & Botstein, D.; Cluster analysis and display of genome-wide expression patterns; *Proc Natl Acad WSci USA* 95, pp. 14863-14868; 1998.

Mootha, V.K. et al.; PGC-1alpha-responsive genes involved in oxidative phosphorylation are coordinately downregulated in human diabetes; *Nat Genet* 34; pp. 267-273; 2003.

Rhodes, D.R. & Chinnaiyan, A.M.; Integrative analysis of the cancer transcriptome; *Nat GenetI*; 37 Suppl, pp. S31-S37; 2005.

Rhodes, D.R. et al.; Mining for regulatory programs in the cancer transcriptome; *Nat Genet* 37; pp. 579-583; 2005.

Segal, E., Friedman, N., Koller, D. & Regev A.; A module map showing conditional activity of expression modules in cancer; *Nat Genet* 36; pp. 1090-1098; 2004.

Subramanian, A. et al.; Gene set enrichment analysis: a knowledge-based approach for interpreting genome-wide expression profiles; *Proc Natl Acad Sci U S.A.*; 103; pp. 15545-15550; 2005.

Tomlins, S.A. et al.; Integrative molecular concept modeling of prostate cancer progression; *Nat Genet* 39,pp. 41-51; 2007.

Cover, T.M. & Thomas, J.A.; *Elements of information theory*; xxiii, p. 748 (Wiley-Interscience; Hoboken, NJ); 2006.

Varadan, V. & Anastassiou, D.; Inference of disease-related molelcular logic from systems-based microarray analysis; *PLoS comput Biol* 2; pp. e681 2006.

Varadan, V., Miller, D.M., $3^{rd}$ & Anastassiou, D.; Computational inference of the molecular logic for synaptic connectivity in C. elegans 22; pp. e497-e506; 2006.

Singh, D. et al.; Gene expression correlates of clinical prostate cancer behavior; *Cancer Cel 1*, pp. 203-209; 2002.

Farias, E.F., Marzan, C. & Mira-y-Lopez, R.; Cellular retinol-binding protein-I inhibits PI3K/Akt signaling through a retinoic acid receptor-dependent mechanism that regulates p. 85-p. 110 heterodimerization; *Oncogene* 24; pp. 1598-1606; 2005.

Irizarry, R.A. et all; Exploration, normalization, and summaries of high density oligonucleotide array probe level data; *Biostatistics* 4, pp. 249-264; 2003.

International Search Report—Application No. PCT/US2006/061749 (Feb. 5, 2008).

International Search Report—Application No. PCT/US2007/06866 (Aug. 5, 2008).

U.S. Appl. No. 12/307,694, Sep. 20, 2011 Non-Final Office Action.
U.S. Appl. No. 12/022,862, Sep. 6, 2011 Notice of Allowance.
U.S. Appl. No. 12/022,862, Jun. 9, 2011 Response to Non-Final Office Action.
U.S. Appl. No. 12/022,862, Nov. 23, 2011 Issue Fee payment.
U.S. Appl. No. 12/307,694, Jan. 19, 2012 Response to Non-Final Office Action.

* cited by examiner

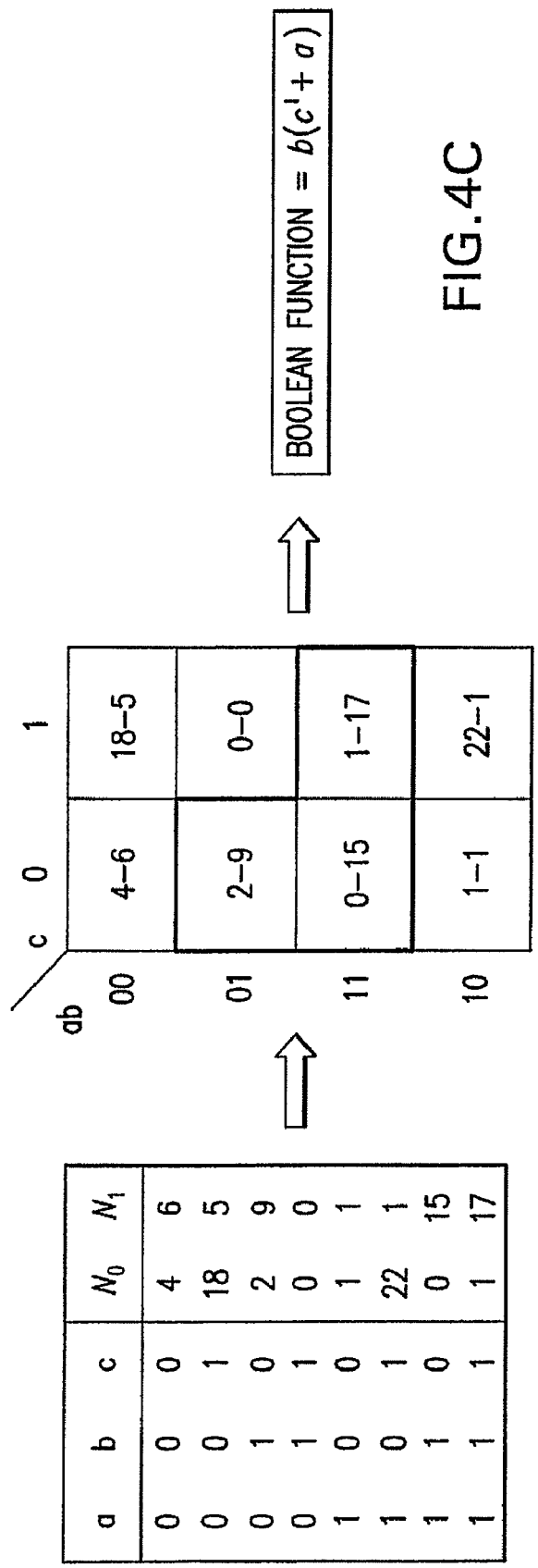

THRESHOLD=30

| ab\c | 0 | 1 |
|---|---|---|
| 00 | 3-9 | 21-2 |
| 01 | 0-37 | 7-0 |
| 11 | 0-4 | 0-0 |
| 10 | 11-0 | 8-0 |

GENES = { a=SPINK2, b=TMSL8, c=RBP1 }

CANCER OCCURS IN THE SIMULTANEOUS ABSENCE OF RBP1 AND PRESENCE OF TMSL8

BOOLEAN FUNCTION = $bc'$
NUMBER OF ERRORS = 11
CLASSIFICATION ACCURACY = 89.22%

FIG.6A

THRESHOLD=45

| ab\c | 0 | 1 |
|---|---|---|
| 00 | 9-0 | 18-0 |
| 01 | 0-0 | 2-0 |
| 11 | 3-0 | 1-1 |
| 10 | 1-50 | 16-1 |

GENES = { a=HPN, b=ENTPD1, c=NELL2 }

CANCER OCCURS IN THE SIMULTANEOUS PRESENCE OF HPN AND ABSENCE OF BOTH NELL2 AND ENTPD1

BOOLEAN FUNCTION = $ab'c'$
NUMBER OF ERRORS = 3
CLASSIFICATION ACCURACY = 97.06%

FIG.6B

THRESHOLD=60

| ab\c | 0 | 1 |
|---|---|---|
| 00 | 25-0 | 9-1 |
| 01 | 1-51 | 4-0 |
| 11 | 9-0 | 0-0 |
| 10 | 2-0 | 0-0 |

GENES = { a=HCF4, b=HPN, c=PGM1 }

CANCER OCCURS IN THE SIMULTANEOUS PRESENCE OF HPN AND ABSENCE OF BOTH NCF4 AND PGM1

BOOLEAN FUNCTION = $a'bc'$
NUMBER OF ERRORS = 2
CLASSIFICATION ACCURACY = 98.03%

FIG.6C

THRESHOLD=75

| ab\c | 0 | 1 |
|---|---|---|
| 00 | 0-2 | 17-0 |
| 01 | 9-0 | 15-0 |
| 11 | 0-15 | 7-3 |
| 10 | 0-22 | 2-10 |

GENES = { a=HPN, b=MCM3AP, c=GSTP1 }

CANCER OCCURS IN THE SIMULTANEOUS PRESENCE OF HPN AND ABSENCE OF EITHER GSTP1 OR MCM3AP

BOOLEAN FUNCTION = $a(c' + b')$
NUMBER OF ERRORS = 7
CLASSIFICATION ACCURACY = 93.14%

FIG.6D

THRESHOLD=90

| ab\c | 0 | 1 |
|---|---|---|
| 00 | 1-48 | 30-0 |
| 01 | 1-0 | 6-2 |
| 11 | 0-0 | 1-0 |
| 10 | 11-0 | 0-2 |

GENES = { a=HLA-DQB1, b=FNBP1, c=DF }

CANCER OCCURS IN THE SIMULTANEOUS ABSENCE OF DF, HLA-DQB1, FNBP1

BOOLEAN FUNCTION = $a'b'c'$
NUMBER OF ERRORS = 5
CLASSIFICATION ACCURACY = 95.10%

FIG.6E

SYSTEM AND METHOD FOR MULTIPLE-FACTOR SELECTION

CROSS-REFERENCE TO RELATED APPLICATIONS

This application is a continuation of International Application PCT/US06/61749, filed Dec. 7, 2006, which claims priority to U.S. Provisional Application Ser. No. 60/748,662 filed Dec. 7, 2005 and U.S. Provisional Application Ser. No. 60/754,102 filed Dec. 27, 2005, the entire contents of each are incorporated by reference herein.

BACKGROUND

The disclosed subject matter relates generally to techniques for factor selection, including factors useful in gene express analysis.

The expression levels of thousands of genes, measured simultaneously using DNA microarrays, may provide information useful for medical diagnosis and prognosis. However, gene expression measurements have not provided significant insight into the development of therapeutic approaches. This can be partly attributed to the fact that while traditional gene selection techniques typically produce a "list of genes" that are correlated with disease, they do not reflect any interrelationships of the genes.

Gene selection techniques based on microarray analysis often involve individual gene ranking depending on a numerical score measuring the correlation of each gene with particular disease types. The expression levels of the highest-ranked genes tend to be either consistently higher in the presence of disease and lower in the absence of disease, or vice versa. Such genes usually have the property that their joint expression levels corresponding to diseased tissues and the joint expression levels corresponding to healthy tissues can be cleanly separated into two distinct clusters. These techniques are therefore convenient for classification purposes between disease and health, or between different disease types. However, they do not identify systems of multiple interacting genes, whose joint expression state predicts disease.

There is therefore a need for an approach that identifies modules of genes that are jointly associated with disease from gene expression data. There is also a need to for an approach that will provide insight into the underlying biomolecular logic by producing a logic function connecting the combined expression levels in a gene module with the presence of disease.

SUMMARY

The disclosed subject matter provides techniques for multiple-factor selection. The factors can be features or elements that are jointly associated with one or more outcomes by their joint presence or absence. There may be a non-causative correlation between the factors, features, or elements and the outcomes.

In some embodiments, Entropy Minimization and Boolean Parsimony (EMBP) is used to identify modules of genes jointly associated with disease from gene expression data, and a logic function is provided to connect the combined expression levels in each gene module with the presence of disease. The smallest module of genes whose joint expression levels can predict the presence of disease can be identified.

In accordance with an aspect of the disclosed subject matter, the simplest logic function connecting these genes to achieve this prediction can be identified. In one example, EMBP analysis can be applied on a prostate cancer dataset, and the resulting gene modules and logic functions are validated on a different dataset.

In one embodiment, the disclosed subject matter provides a method for selecting factors from a data set of measurements where the measurements include values of the factors and outcomes. Two or more factors that are jointly associated with one or more outcomes are identified from the data set, and each of the factors are analyzed to determine at least one interaction among the factors with respect to an outcome.

The two or more factors can be a module of factors, and the at least one interaction can be a structure of interactions. Preferably, the at least one interaction is a logic function.

In another embodiment, the two or more factors are two or more genes, the data can be gene expression data including expression levels, and the one or more outcomes can be presence or absence of a disease. The two or more genes can be a module of genes, and such that the smallest module of genes with joint expression levels are used for a prediction of the presence or absence of disease with high accuracy. Further, the logic function can be the simplest logic function connecting the genes to achieve the prediction.

In another embodiment, a method for gene selection can be provided. The method can be used for selecting two or more genes from gene expression data, the gene expression data including expression levels for each of the two or more genes. The method includes providing gene expression data for two or more genes, where the gene expression data includes expression levels for each of the tow or more genes. The method also includes discretizing the gene expression data, identifying the two or more genes with a minimal conditional entropy and identifying an interaction that connects the expression levels in the two or more genes with presence of a disease. The gene expression data can be derived from a microarray of gene expression data, or, alternatively, the two or more genes can be a module of genes. Preferably, the interaction is the most parsimonious Boolean function.

In another embodiment, a system for selecting two or more genes from gene expression data, the gene expression data including expression levels for each of the two or more genes, is provided. The system includes at least one processor coupled to a computer readable medium, the computer readable medium storing instructions which when executed cause the processor to provide gene expression data for the two or more genes, discretize the gene expression data, choose a single threshold for each of the two or more genes, identify the two or more genes with a minimal conditional entropy, and identify an interaction that connects the expression levels in the two or more genes with presence of a disease. In this embodiment, the gene expression data includes expression levels for each of the two or more genes.

BRIEF DESCRIPTION OF THE DRAWINGS

FIGS. 4(A)-4(C) are illustrative drawings showing one example of an estimation of a Boolean function for a gene module.

FIGS. 6(A)-6(E) are Karnaugh maps leading to Boolean functions across different thresholds.

DETAILED DESCRIPTION

Figure 1:
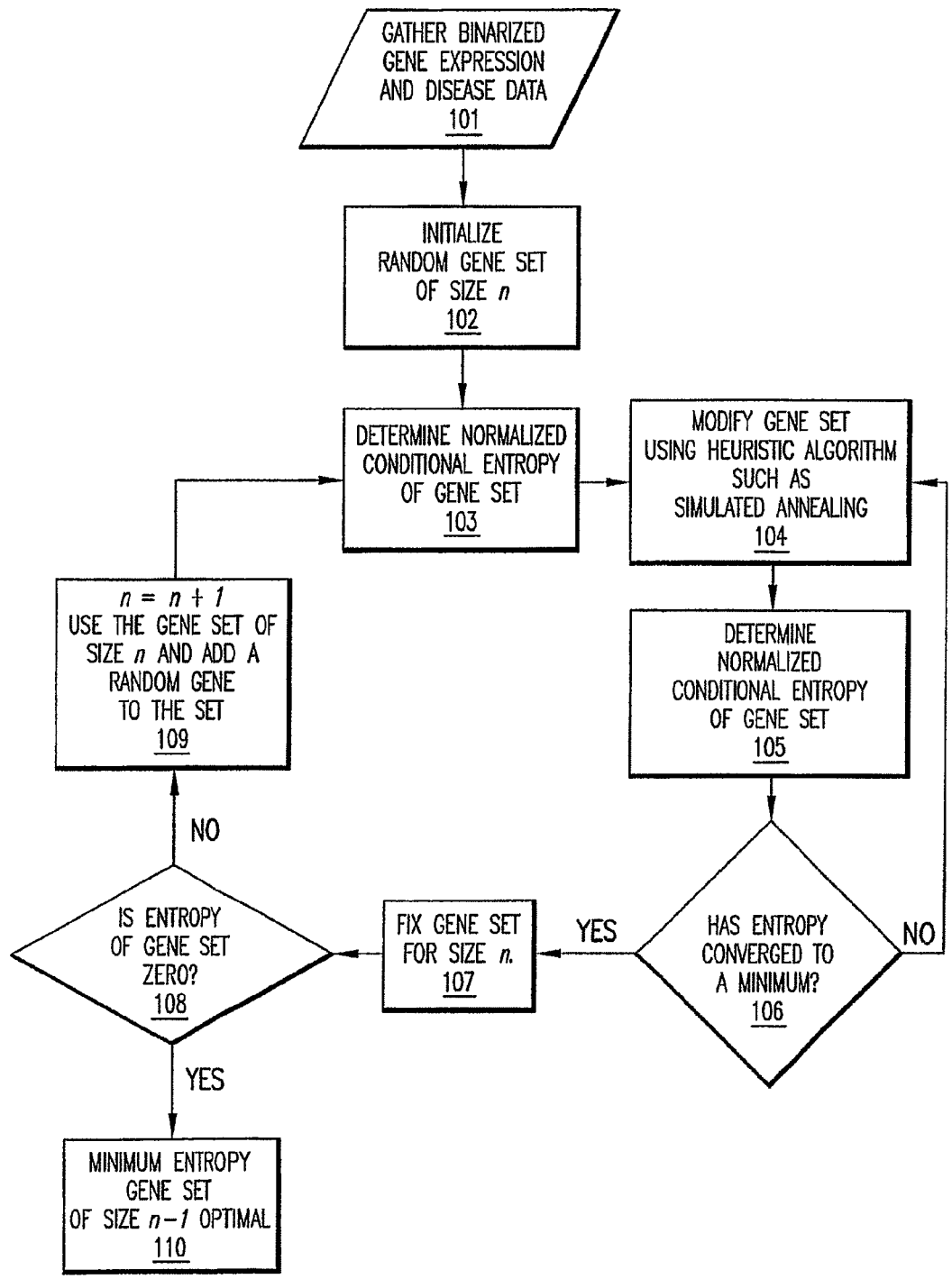
FIG. 1 is an illustrative drawing of entropy minimization.

According to one aspect of the disclosed subject matter, a method for multiple factor selection is provided. The method includes identifying factors jointly associated with an outcome from a data set for a plurality of factors, and analyzing each of the plurality of modules to determine a structure of interactions among the factors with respect to the outcome. The data set can be a set of measurements that includes values of the factors and the outcome.

One important application of the disclosed subject matter, which will be described in detail below is for the inference of disease-related molecular logic from a systems-based microarray of gene data. Although the following will be described for disease data it can be more generally applicable to other data sets. Other applicable data sets include other biological data such as how cells are influenced by stimuli jointly, financial data, internet traffic data, scheduling data for industries, marketing data, and manufacturing data, for example. Table 1, below, specifies other data sets relevant to various objectives, including factors and outcomes, to which the disclosed subject matter can also be applied:

TABLE 1

| Objective | Factors | Outcomes |
|---|---|---|
| Disease pathway identification | Gene expression | Disease |
| Synaptic specificity factors | Gene expression | Neural synapses |
| Disease susceptibility of specific genotypes | Single Nucleotide Polymorphisms (SNPs) | Disease |
| Genotypic basis for gene expression profiles | SNPs | Gene expression |
| Gene regulation factors | Gene expression | Gene expression |
| Gene expression association with individual SNPs | Gene expression | SNP |
| Pharmacogenomics | SNPs | Drug resistance |
| Drug side-effect modeling | SNPs | Side effect of drug |
| Stocks/bonds/currency selling/buying price identification | Stocks/bonds/currency price time series data | Sell/Buy at given price |
| Macroeconomic models | Macroeconomic time series such as consumer index, housing market index, trade balance, etc | Federal interest rate increase/decrease |

In accordance with the disclosed subject matter, microarray expression data is discretized. For example, the data can be binarized into two levels. Although the EMBP methodology can be generalized to account for multiple expression levels, the binarization of expression data simplifies the presentation of the concepts and provides simple logical functions connecting the genes within the found modules. Other levels of discretization, such as trinarization, can also be used.

Rather than independently binarizing each gene's expression level, which would be more appropriate for an individual gene ranking approach, single thresholds are used for the genes. This approach is consistent with the fact that finding global interrelationships among genes desirable for researchers and that the microarray data have already been normalized across the tissues and genes. Therefore, a choice of high threshold will identify the genes that are "strongly" expressed, while a choice of a low threshold will identify the genes that are expressed even "weakly." EMBP analysis can be performed across several thresholds and to determine the threshold levels that provide optimized performance, as described below.

Following binarization, each gene can be assumed to be either expressed or not expressed in a particular tissue. It can also be assumed that there are two types of tissues, either healthy ones or tissues suffering from a particular disease. The latter assumption can also be generalized to include more than two types of tissues, or modified to be used for classification among several types of cancer. Thus, given M genes and K tissues, an M×K binary "expression matrix" E can be defined so that a E(i,j) is 1 if gene i is expressed in tissue j, and 0 otherwise. Furthermore, a K-vector c can be defined so that c(j) is 1 if tissue j is diseased and 0 if it is healthy.

For each gene module of size n there are $2^n$ possible gene expression states. For each state S the number $N_0(S)$ of times that the state appears in a healthy tissue can be counted, and the number of times $N_1(S)$ that it appears in a diseased tissue can also be counted. A table can be created with $2^n$ rows corresponding to the gene expression states (a "state-count table"), in which each row contains the two counts $N_0$ and $N_1$ for the corresponding state. Table 2, illustrates two examples of such state-count tables for n=4.

TABLE 2

| a | b | c | d | $N_0$ | $N_1$ | a | b | c | d | $N_0$ | $N_1$ |
|---|---|---|---|---|---|---|---|---|---|---|---|
| 0 | 0 | 0 | 0 | 0 | 0 | 0 | 0 | 0 | 0 | 0 | 14 |
| 0 | 0 | 0 | 1 | 0 | 0 | 0 | 0 | 0 | 1 | 5 | 0 |
| 0 | 0 | 1 | 0 | 0 | 0 | 0 | 0 | 1 | 0 | 8 | 0 |
| 0 | 0 | 1 | 1 | 0 | 0 | 0 | 0 | 1 | 1 | 2 | 0 |
| 0 | 1 | 0 | 0 | 0 | 0 | 0 | 1 | 0 | 0 | 1 | 19 |
| 0 | 1 | 0 | 1 | 1 | 0 | 0 | 1 | 0 | 1 | 0 | 13 |
| 0 | 1 | 1 | 0 | 12 | 21 | 0 | 1 | 1 | 0 | 0 | 2 |
| 0 | 1 | 1 | 1 | 10 | 10 | 0 | 1 | 1 | 1 | 0 | 1 |
| 1 | 0 | 0 | 0 | 0 | 0 | 1 | 0 | 0 | 0 | 4 | 0 |
| 1 | 0 | 0 | 1 | 2 | 1 | 1 | 0 | 0 | 1 | 12 | 0 |
| 1 | 0 | 1 | 0 | 0 | 0 | 1 | 0 | 1 | 0 | 4 | 0 |
| 1 | 0 | 1 | 1 | 0 | 0 | 1 | 0 | 1 | 1 | 6 | 0 |
| 1 | 1 | 0 | 0 | 0 | 0 | 1 | 1 | 0 | 0 | 1 | 3 |
| 1 | 1 | 0 | 1 | 8 | 3 | 1 | 1 | 0 | 1 | 2 | 0 |
| 1 | 1 | 1 | 0 | 2 | 1 | 1 | 1 | 1 | 0 | 0 | 0 |
| 1 | 1 | 1 | 1 | 15 | 16 | 1 | 1 | 1 | 1 | 5 | 0 |
| H = 0.951 | | | | | | H = 0.088 | | | | | |

Referring to FIG. 1, a method for identifying the set of n genes whose combined expression levels predicts the presence or absence of disease with minimum uncertainty will be described.

This can be referred to as "entropy minimization," because the uncertainty can be quantified with the information theoretic measure known as conditional entropy. A probabilistic model can be created, in which probabilities are equal to relative frequencies derived from the counts $N_0(S)$ and $N_1(S)$, so that the presence of disease and the gene expression states are random variables.

Specifically, the probability of encountering expression state S in a tissue chosen at random can be defined as P(S) according to Equation (1):

$$P(S) = \frac{N_0(S) + N_1(S)}{K} : \begin{array}{l} \text{Probability of encountering expression} \\ \text{state } S \text{ in a tissue chosen at random} \end{array} \quad (1)$$

Additionally, the probability of disease in the tissue given that its expression state S can be defined as Q(S) according to Equation (2):

$$Q(S) = \frac{N_1(S)}{N_0(S) + N_1(S)} : \begin{array}{l}\text{Probability of disease in a tissue} \\ \text{given that its expressing state is } S\end{array} \quad (2)$$

If the expression state S for a particular tissue is known, then the uncertainty of determining whether or not disease exists in that tissue can be measured by the entropy H(Q(S)), where the function H can be defined by Equation (3):

$$H(q) = -q\log_2(q) - (1-q)\log_2(1-q) \quad (3)$$

The average overall uncertainty of determining whether or not disease is present can then be measured by the "conditional entropy" of the presence of disease given the expression state for the gene set, defined as by Equation (4):

$$\Sigma P(S) H(Q(S)) \quad (4)$$

The summation is over the 2 states S with P(S)>0. Finally, to ensure that the range of possible values for the conditional entropy extends from 0 to 1, normalization can be performed by dividing by H($Q_{null}$), the entropy corresponding to the probability of disease in a randomly chosen tissue. In the case of the prostate data that is used, this probability is equal to 52/102. For simplicity, in the specification, the normalized conditional entropy is often referred to as just "entropy."

The conditional entropy, as defined above, depends on the counts $N_0$ and $N_1$ and for the $2^n$ states. Its interpretation as a measure of uncertainty is illustrated in the example of Table 2, which contains two state-count tables which were created using the binarized expression matrix for prostate tissues used in this paper, and a threshold of 15. The state-count table on the left corresponds to a choice of four genes a, b, c, d, selected at random, which in this case happen to have accession numbers a: AF038193, b: M22632, c: X87949, d: AI926989. The resulting value of the normalized conditional entropy of 0.951 is typical for random choices of gene sets. On the other hand, the state-count table on the right corresponds to the gene set for which the minimum normalized conditional entropy of 0.088 was found, consisting of genes a: COL4A6, b: CYP1B1, c: SERPINB5, and d: GSTP1, to be discussed below. In this latter gene set choice, as shown in Table 2, the reduced entropy is manifested by the fact that the statistics are skewed for nearly all states. For example, all 13 tissues corresponding to state 0101 are cancerous, and all 12 tissues corresponding to state 1001 are healthy.

Entropy minimization can be directed to identifying the gene set with the minimum conditional entropy, as defined above, among the subsets of size n of the full set of M genes. The number of these subsets is equal to:

$$\binom{M}{n} \quad (5)$$

and becomes large for n≧3, making the exhaustive search method impractical. As explained below, however, this can be addressed using heuristic search optimization methods 104.

A combination of two heuristic optimization techniques can be used to search for minimum entropy gene sets, allowing sufficient time for each of them to converge. The first technique is depicted in FIG. 1. Initially, the binarized gene expression and disease data is gathered 101. Then, starting from a randomly chosen gene set of size n 102, the normalized conditional entropy of the gene set is determined. The gene set is then modified using a heuristic algorithm such as simulated annealing 104 and the normalized conditional entropy of the gene set is again determined 105. If the entropy has not converged to a minimum 106, features 104 and 105 are repeated. If the entropy has converged to a minimum 106, the gene set size n is fixed 107. If the entropy of the current gene set is zero 108, the minimum entropy gene set of size n−1 is optimal 110. If the entropy of the gene set at this point is not zero 108, the "current" gene set is modified by replacing one of its genes, chosen at random, with a new gene, also chosen at random from the entire gene set M such that the size n of the new gene set is increased to the size of the current gene set plus one (n=n+1) 109. Features 103-108 are then repeated for the new gene set. If the conditional entropy 103, 105 of the new gene set is lower than that of the current gene set, then the new gene set replaces the current gene set. The process terminates when the conditional entropy is zero 108, 110, or when the current gene set remains unmodified for a large number of times 106.

Traditional optimization methodology is used. The number of iterations can range from 10 to 100 or more. To avoid selecting a local minimum, the same iterative algorithm can be repeated several times starting from different initial conditions of the same size and select the gene set that yields the overall lowest conditional entropy. The size of the gene set can then be increased 109 to n+1, and the whole process repeated, making sure that one of the chosen initial conditions contains the previously found gene set. This technique converges to some choice of near-optimum results.

In order to reduce the chance that the found solution corresponds to a local, rather than a global minimum, a Simulated Annealing (SA) approach can be used to search in the space of the subsets of size n. In an "annealing" process, a melt, initially disordered at high "temperatures," can be slowly cooled. As cooling proceeds, the system becomes more ordered and approaches a "frozen" state when the temperature equals zero.

As applied to the gene data set, at high temperatures the algorithm modifies the "current" gene set of size n by replacing k genes, chosen at random, with k new genes (k<n). If the new gene set has lower entropy compared to the current gene set, it is chosen to replace the current gene set. However, with a small probability also proportional to the current temperature, small increases in the entropy are allowed. As the temperature falls over time, the value of k keeps dropping, effectively searching in the local neighborhood of the gene set. The SA algorithm terminates when the temperature reaches zero or when the current gene set remains unmodified for a larger number of iterations.

Changing multiple genes at high temperatures once allows the algorithm to search for solutions across large regions of the state space. However, as the temperature falls, the algorithm searches in increasingly localized regions thus allowing for "fine tuning" of the solution.

The entropy minimization techniques can be implemented by way of off-the-shelf software such as MATLAB, JAVA, C++, or any other software. Machine language or other low level languages can also be utilized. Multiple processors working in parallel can also be utilized.

Figure 2:
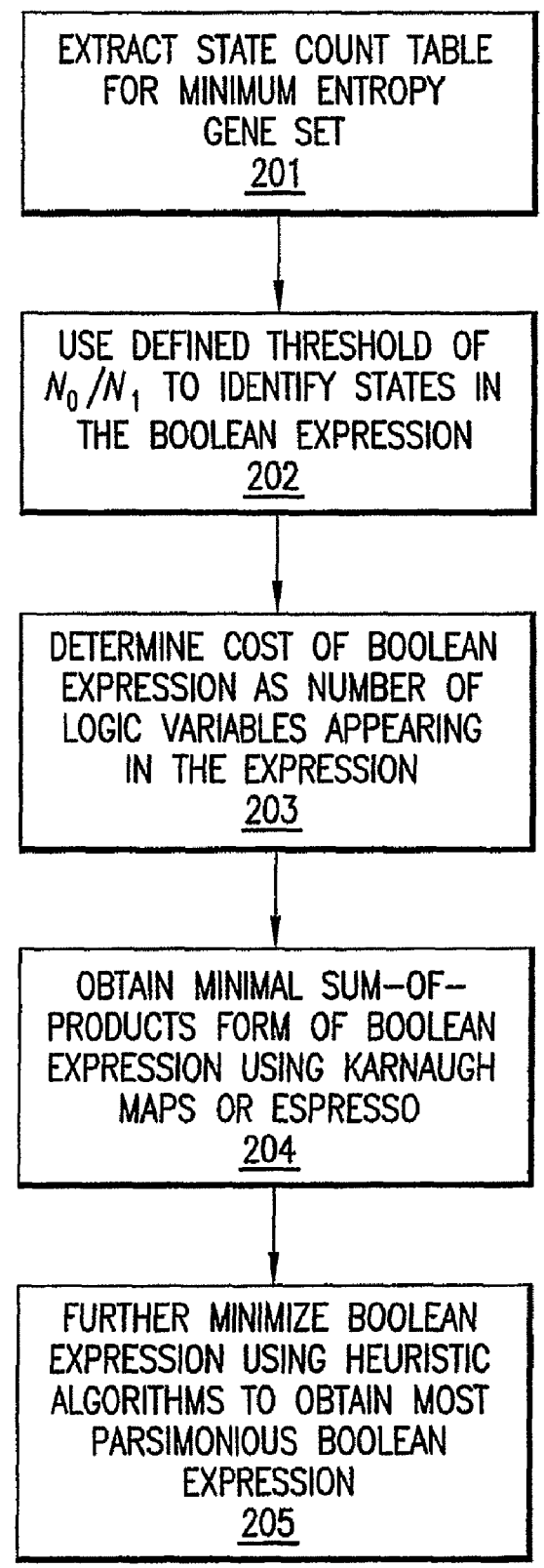
FIG. 2 is an illustrative drawing of boolean parsimony.

Once the minimum entropy gene set is identified, then the state-count table is extracted 201, as shown in FIG. 2. If the conditional entropy for a particular gene set is found to be exactly zero, this implies that the joint expression levels of the members of that gene module determine the existence of disease with absolute certainty under the assumption of the probabilistic model derived from the relative frequencies.

This happens whenever, for the $2^n$ states in the corresponding state-count table, at least one of the counts $N_0$ and $N_1$ is zero.

In practice, when this occurs, a large number of states are encountered occasionally. A reliable association of disease based on these rarely encountered states cannot be made, and including them in the model will result in "overfitting," so they are treated as noise and are ignored, in favor of the states which predominantly correspond to disease. In accordance with the disclosed subject matter, the definition for such states can be that they have been encountered at least three times and that the number of corresponding cancerous tissues can be at least four times larger than the count of corresponding healthy tissues, i.e., $N_1 \geq 3$ and $N_1 \geq N_0$. Note that other definitions can be used, as needed. Logic functions or relationships are useful because they can lead to biological discovery when understood in the context of additional biological knowledge. Therefore, whenever the entropy for a gene set is found to be exactly zero, the size of the gene set can be decreased by one, and the minimum-entropy gene set of that size can be selected. Thus, the output of the EMBP analysis contains a gene module for which the conditional entropy can be close, but not equal, to zero.

Once a gene module has been identified, and the expression states 202 for that module, as shown in FIG. 2, that are predominantly associated with cancer have been determined as described above, the following can be then addressed: given the gene expression states associated with disease, find the simplest logical rule that connects the expression levels in the gene module with the presence of disease, as depicted in FIG. 2.

This can be referred to as "Boolean parsimony", because the logical rule will be identified by the "most parsimonious Boolean function." The definition for this logic function is one containing the operators AND, OR and NOT, which minimizes a "cost," defined as the total number of logic variables appearing in the expression 203. The most parsimonious function is one which is essentially the least complex because it "costs" the least 205.

In Boolean algebra, each logic variable can take the value of either 0 (false) or 1 (true), the operator AND corresponds to multiplication, and the operator OR corresponds to addition. The symbol of prime (') following the logic variable designates the operator NOT. For example, ab+a'b'+ab' means (a AND b) OR [(NOT a) AND (NOT b)] OR [a AND (NOT b)] and the "cost" (as defined above) of this Boolean function is 6, because each of the variables a and b appears three times 203. This Boolean expression happens to be logically equivalent to a+b', meaning: a OR (NOT b). The latter expression is more parsimonious than the former, because its "cost" is equal to 2, as each of the letters a and b appears once.

The reason for using Boolean parsimony is that the biological role of each gene becomes more immediately clear if the Boolean expression contains the corresponding logic variable either once or a few times. The above definition of Boolean parsimony was selected because the logic functions AND, OR and NOT often have straightforward potential biological interpretations. The issue can be easily resolved manually when the size of the gene set is less than five, using Karnaugh map logic design methodology (as shown in FIGS. 6A-6E). Otherwise, Boolean minimization programs such as Espresso can be used 204. Most of them retain the "sum of products" structure of the Boolean expression, but further minimization is desirable and possible using heuristic algorithms.

Figure 3:
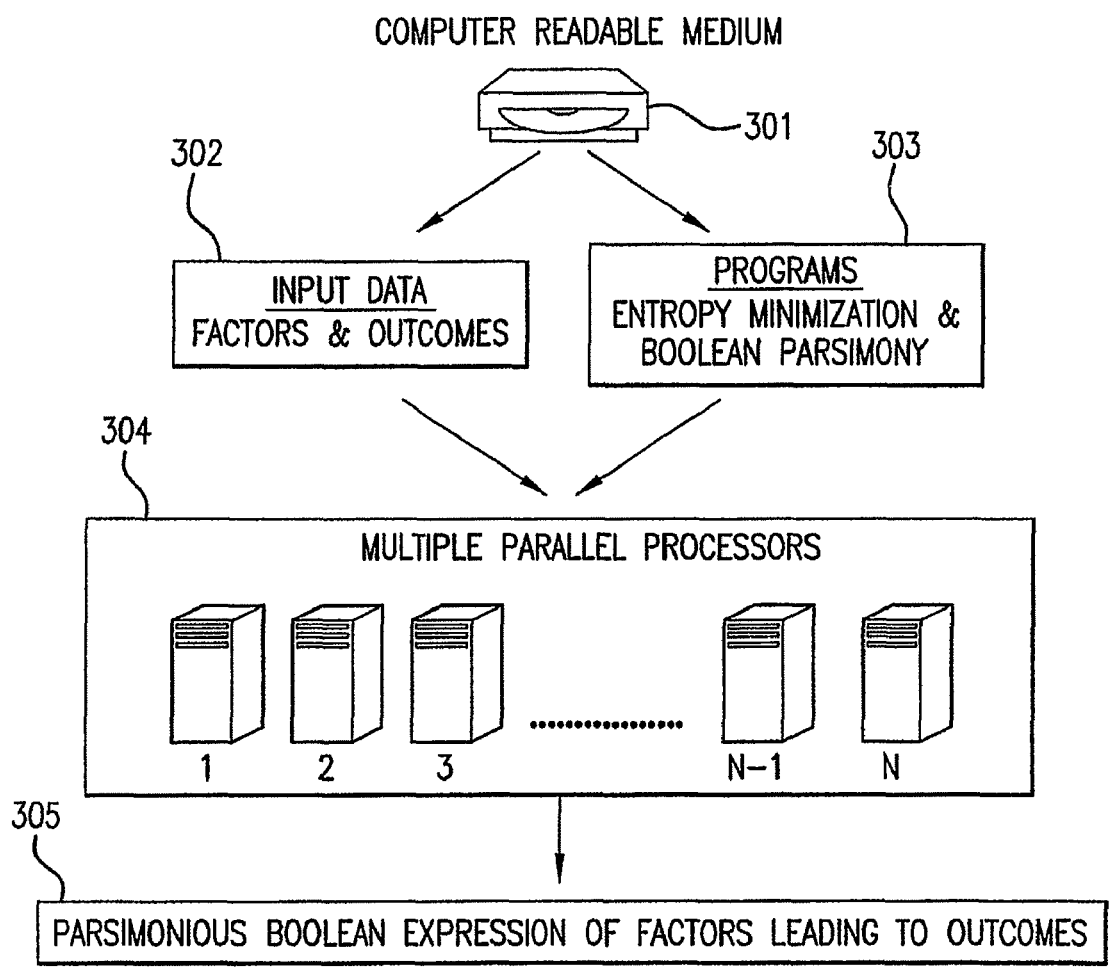
FIG. 3 is an illustrative drawing of the disclosed subject matter.

As illustrated in the embodiment depicted in FIG. 3, a system in accordance with the disclosed subject matter can include a processor or multiple processors 304 and a computer readable medium 301 coupled to the processor or processors 304. The computer readable medium includes data such as factors and outcomes 302 and can also include programs for entropy minimization and boolean parsimony 303. The system leads to a parsimonious boolean expression of factors that relate to outcomes 305. Multiple processors 304 working in parallel can also be utilized.

FIGS. 4(A)-4(C) are illustrative drawings showing one example of an estimation of a Boolean function for a gene module.

In one embodiment of the disclosed subject matter, two different prostate cancer datasets are used. The first prostate cancer microarray expression data contains gene expression profiles for 102 prostate tissues, of which 52 are cancerous and 50 are healthy, available at genome.wi.mit.edu/MPR/prostate. The gene expression profiles in scaled average difference units are produced using HG-U95A Affymetrix microarrays with probes for 12,600 genes. This dataset will henceforth be referred to as the "EMBP dataset," because it can be used to apply EMBP analysis. A second independently derived dataset, also containing scaled average difference units referring to 34 tissue samples, out of which 25 are cancerous and 9 are healthy can be also obtained at gnf.org/cancer/prostate and used for validating the gene modules and logic functions estimated over the EMBP dataset. This latter dataset will be referred to as the "validation dataset."

The continuous-valued data of the EMBP dataset can be binarized using several thresholds ranging from −30 to 225 in increments of 15 and estimated the minimum entropy gene modules for each of them. For each threshold value gene modules of size n=1, 2, 3 and 4 were considered. For n=4, the entropy values occasionally went down to precisely zero due to overfitting. On the other hand, several gene sets of size 3 with entropy values less than 0.20, which is low—note that H(0.97)=0.20, meaning that if the conditional entropy is 0.20 then, on the average, each state is associated with either cancer or health with probability 97%. Therefore, n=3 was selected to be the number of genes included in these gene modules.

Figure 5A:
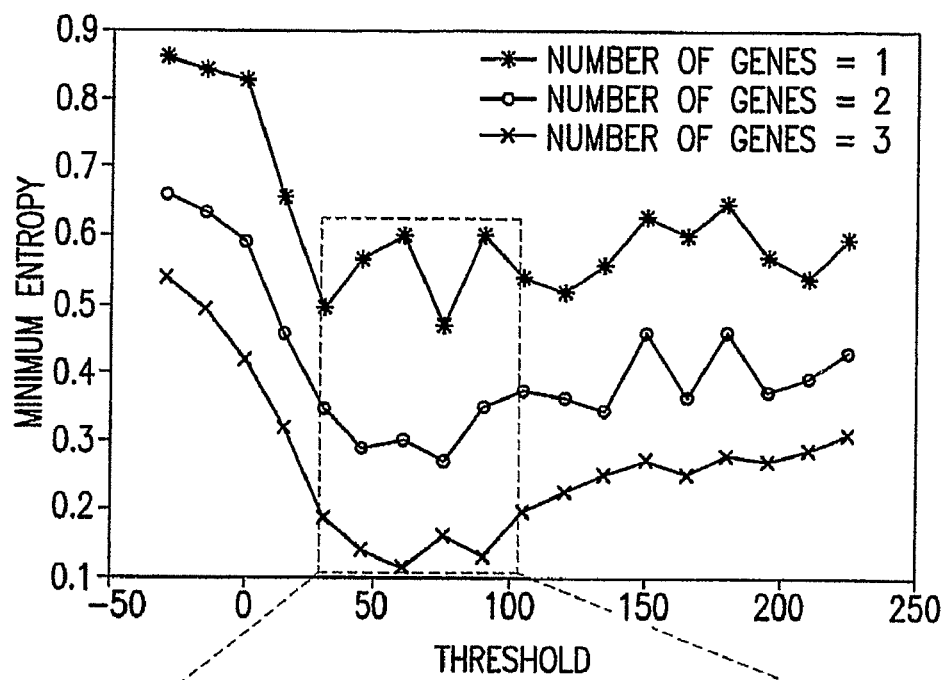
FIG. 5(A) and FIG. 5(B) are graphs representing minimum entropy across different thresholds.

The results of are shown in FIG. 5A. The thresholds for which the minimum entropy values were below 0.20 for n=3 are 30, 45, 60, 75 and 90. The minimum entropy gene modules for these thresholds along with their entropies are listed in Table 3, below.

TABLE 3

|  | Gene Module | | | |
| --- | --- | --- | --- | --- |
| Threshold | a | b | c | Entropy |
| 30 | SPINK2 | TMSL8 | RBP1 | 0.19155 |
| 45 | HPN | ENTPD1 | NELL2 | 0.14302 |
| 60 | NCF4 | HPN | PGM1 | 0.11587 |
| 75 | HPN | MCM3AP | GSTP1 | 0.16287 |
| 90 | HLA-DQB1 | FNBP1 | DF | 0.13267 |

In the following example, official gene symbols are used, and Table 4, below, contains a legend with the corresponding accession numbers, aliases and brief gene descriptions.

TABLE 4

| Symbol | Accession | Alias/Description |
| --- | --- | --- |
| COL4A6 | D21337 | Collagen, type IV, alpha 6 |
| CYP1B1 | U03688 | Cytochrome P450, family 1, subfamily B, polypeptide 1 |
| DF | M84526 | Adipsin, D component of complement |

TABLE 4-continued

| Symbol | Accession | Alias/Description |
|---|---|---|
| ENTPD1 | AJ133133 | Ectonucleoside triphosphate diphosphohydrolase 1 |
| FNBP1 | AB011126 | KIAA0554, Formin binding protein 1 |
| GSTP1 | U12472 | Glutathione S-transferase pi |
| HLA-DQB1 | M81141 | Major histocompatibility complex, class II, DQ beta 1 |
| HPN | X07732 | Hepsin, transmembrane protease, serine 1 |
| HIST1H1E | M60748 | H1F4, Histone 1, H1e |
| KRT6E | L42611 | Keratin 6E |
| MCM3AP | AB011144 | KIAA0572, MCM3 minichromosome maintenance deficient 3 (S. cerevisiae) associated protein |
| NCF4 | AL008637 | P40PHOX, neutrophil cytosolic factor 4 (derived from precise chip probe) |
| NELL2 | D83018 | NEL-like 2 (chicken) protein |
| PGM1 | M83088 | Phosphoglucomutase 1 |
| RBP1 | M11433 | Cellular retinol binding protein 1 |
| SERPINB5 | U04313 | Maspin, Serpin peptidase inhibitor, clade B (ovalbumin), member 5 |
| SPINK2 | X57655 | Serine peptidase inhibitor, Kazal type 2 (acrosin-trypsin inhibitor) |
| TMSL8 | D82345 | TMSNB, Thymosin-like 8 |

Figure 5B:
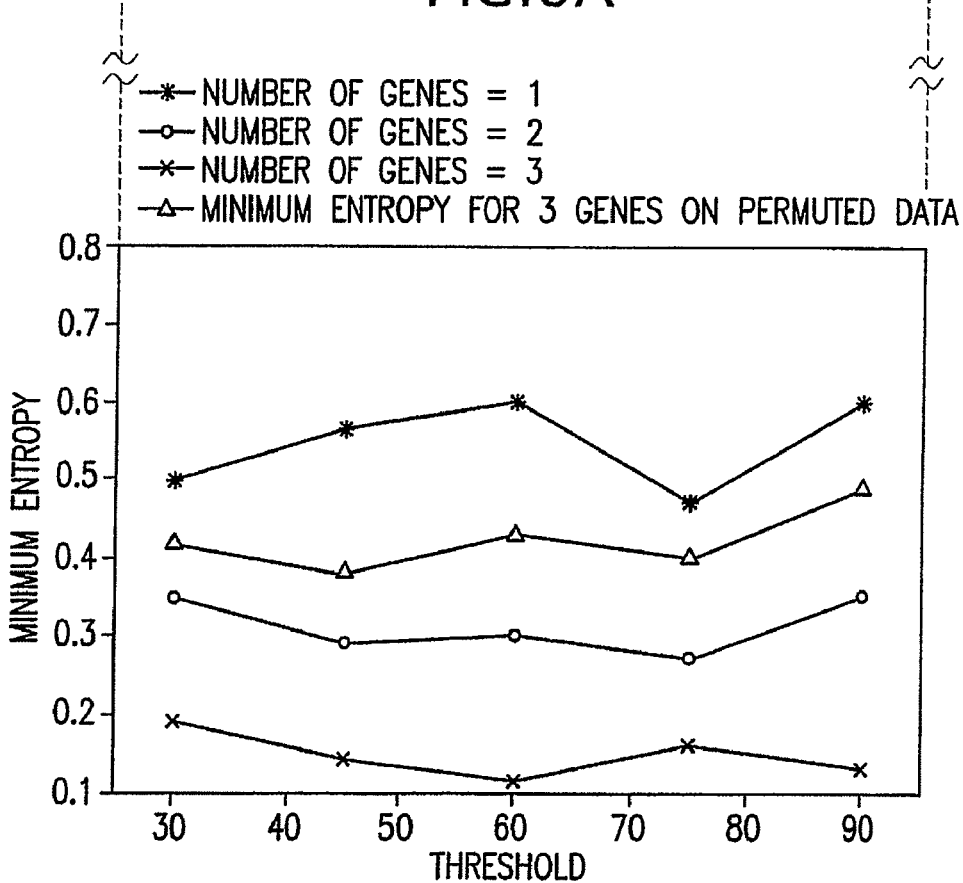
Figure 7:
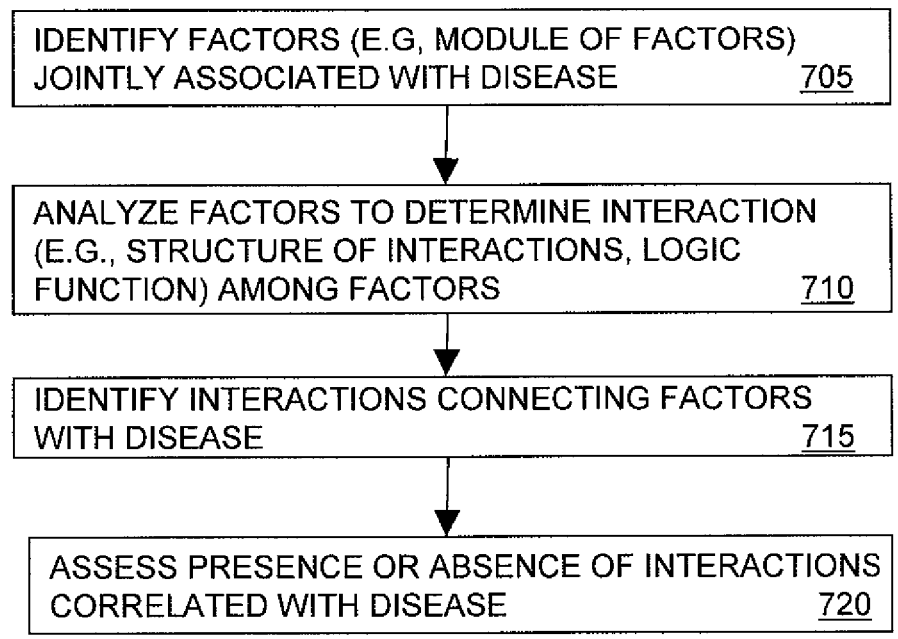
FIG. 7 is a flow chart illustrating a method of predicting the presence of a disease in a subject according to embodiments of the disclosed subject matter.
Figure 8:
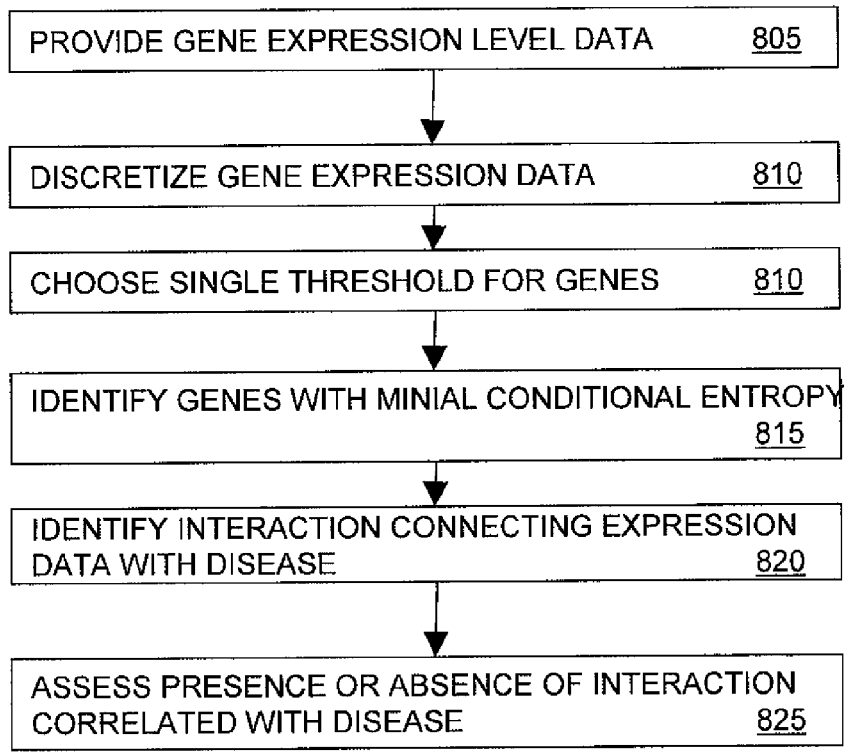
FIG. 8 is a flow chart illustrating a method of predicting the presence of a disease in a subject according to embodiments of the disclosed subject matter.

To evaluate the significance of these minimum entropy values, entropy minimization can be performed over ten random permutations of the tissue class labels. In other words, while keeping the number of healthy and cancerous tissues constant to 50 and 52 respectively, healthy (0) and cancerous (1) labels to the individual tissue profiles are randomly assigned. The entropy minimization algorithm can be performed on the randomly permuted data and the average minimum entropies for n=3 can be estimated for the thresholds 30, 45, 60, 75 and 90 for the same expression matrix of the EMBP dataset. The estimated averages of the entropies are shown in the heavy black line in FIG. 5B. Notably, the entropy values for the randomly permuted data for n=3 are much higher than those estimated on the actual dataset, and even significantly higher than the entropy values of the actual data with n=2, indicating that the gene modules identified by entropy minimization on the actual data have real biological meaning, rather than being due to chance.

The most parsimonious Boolean functions for these five gene modules can then be estimated. FIGS. 6A-6E contain the Karnaugh maps from which the functions are derived, together with the corresponding Boolean functions and their accuracy if these simple functions can be used for classification on the "EMBP dataset." For convenience, these Boolean functions are also formulated in words in FIGS. 6A-6E, where "presence" and "absence" of a gene refer, for simplicity, to the presence or absence of mRNA from the gene. Furthermore, it was found that gene ENTPD1 in FIG. 6B can be replaced by gene HIST1H1E, and that gene NCF4 in FIG. 6C can be replaced by gene KRT6E. In both cases, these substitutions yield identical results.

The genes mentioned in FIGS. 6A-6E should not be seen as individual "prostate cancer-related genes," which, in traditional approaches, are found to be either consistently overexpressed or consistently underexpressed in cancer. Instead, each of the identified genes should be seen as a member of a synergistic gene module, as evidenced by the formulation of the corresponding Boolean function. To further clarify the fundamental difference between the two approaches, the following are provided for each of the five identified gene modules, derived from simple observation of the counts in each Karnaugh map, each of which could provide hints for its biological explanation:

(a) Absence of RBP1, if accompanied by either presence of TMSL8 or absence of SPINK2 is associated with cancer in 50 out of 53 such tissues. However, in the simultaneous absence of TMSL8 and presence of SPINK2, absence of RBP 1 is not associated with cancer. On the contrary all 11 such tissues are healthy.

(b) Presence of NELL2 is associated with health in 37 out of 39 such tissues, even if HPN (normally associated with cancer) is present. Simultaneous presence of HPN and NELL is associated with health in 17 out 19 such tissues.

(c) Presence of NCF4 is associated with health in all 11 such tissues, even if HPN (normally associated with cancer) is present: simultaneous presence of HPN and NCF4 is associated with health in all 9 such tissues. The same formulation is true if NCF4 is replaced by KRT6E.

(d) If either HPN is present or MCM3AP is absent, then the absence of GSTP1 is associated with cancer, as all such 39 tissues are cancerous. However, if HPN is absent and MCM3AP is present, then the absence of GSTP1 is not associated with cancer, as all such 9 tissues are healthy.

(e) In the absence of HLA-DQB1, absence of DF is associated with cancer in 48 tissues out of 50, and presence of DF is associated with health in 36 tissues out of 38. However, in the presence of HLADQB1, absence of DF is instead associated with health, as all 11 such tissues are healthy While the classification performance of the Boolean functions from EMBP analysis is high over the dataset upon which the results were derived (FIGS. 6A-6E), it is important to validate these results over previously unseen gene expression profiles. The five gene modules of FIGS. 6A-6E are tested using their corresponding Boolean functions on the "validation dataset". For that task, the expression levels of the validation dataset are binarized.

A simple transformation of the form y=ax+b was used to map the EMBP dataset thresholds to the validation dataset thresholds, where x represents thresholds over the EMBP dataset and y represents thresholds over the validation dataset. To estimate the coefficients a and b, the gene expression values are averaged over all tissues for the 12,600 genes common to both datasets. Thus two vectors x and y of length 12,600, are obtained whose elements were the mean gene expression levels across the tissues belonging to the EMBP and validation datasets, respectively. These two vectors are used to calculate the least squares estimate for the coefficients a and b. The mean value and the 95% confidence bound for the two coefficients were found to be: a=8.25+/−0.088, b=92.12+/−9.06. The thresholds are transformed using several values of a and b within the 95% confidence bounds, and the values yielding the highest found classification performance are selected, which were a=8.338 and b=92.12. Table 5, below summarizes the results for each of the five Boolean functions outlined in FIG. 6 over the validation dataset.

TABLE 5

| EMBP dataset Threshold | Gene Module a | b | c | Boolean Function | Validation dataset Threshold | Classification Accuracy (%) | Specificity (%) | Sensitivity (%) |
|---|---|---|---|---|---|---|---|---|
| 30 | SPINK2 | TMSL8 | RBP1 | bc' | 342.26 | 85.29 | 77.78 | 88 |
| 45 | HPN | ENTPD1 | NELL2 | ab'c' | 467.33 | 94.12 | 100 | 92 |
| 60 | NCF4 | HPN | PGM1 | a'bc' | 592.40 | 94.12 | 100 | 92 |
| 75 | HPN | MCM3AP | GSTP1 | a(c' + b') | 717.47 | 97.06 | 100 | 96 |
| 90 | HLA-DQB1 | FNBP1 | DF | a'b'c' | 842.54 | 85.29 | 77.78 | 88 |

Remarkably, the classification accuracy of the simple three-gene (two-gene in one case) Boolean functions in the validation dataset were consistently high, exceeding 90% in most cases, indicating that EMBP analysis accurately extracted universally valid prostate cancer-related features.

The genes in the modules resulting from EMBP analysis are not co-regulated, because, if they were, then each of them alone would provide much of the information that all of them provide, therefore a different gene would be a more appropriate partner, as it would provide complementary information. Nevertheless, these genes are typically related by a shared common "theme," in which they are playing synergistic roles. For example, two genes can appear because they are both required for the activation of a particular cancer-causing pathway. The cause-and-effect relationship connecting disease and the presence of particular genes in a gene module is not clear from the results of quantitative analysis alone, and the Boolean functions can be seen as approximations when they are based on a relatively small set of input data, as in this case.

Coupled with additional biological knowledge, however, the results of EMBP analysis can help infer disease-related pathways, which, in turn can help develop therapeutic interventions. This methodology uses the clues provided by the results to create assumptions involving additional genes. Assuming that each gene module has a "story" to tell, the combination of these "stories" into an integrated scenario combining many genes can be attempted. In accordance with an aspect of the disclosed subject matter, two examples of this methodology are presented below.

The first focus is on the three-gene module with the lowest overall conditional entropy (0.1159) (FIG. 6C), consisting of genes {HPN, NCF4, PGM1}. Hepsin (HPN) is a serine protease that is overexpressed in most prostate cancers. Recent evidence indicates that hepsin converts single-chain prohepatocyte growth factor into biologically active two-chain hepatocyte growth factor. The hepatocyte growth factor (HGF) is a ligand for Met, a known proto-oncogene receptor tyrosine kinase, suggesting that this functional link between hepsin and the HGF/Met pathway can be related to tumor progression. Furthermore, HGF protects cell against oxidative stress-induced apoptosis. These results suggest that hepsin may promote tumor progression by inhibiting the apoptotic mechanisms that are normally activated in cells after they become cancerous as a result of damage caused by oxidative stress.

Interestingly, both of the other members of the module (NCF4 and PGM1) have also been related to oxidative stress, strengthening the above hypothesis. Phosphoglucomutase is inhibited under oxidative stress. The absence of PGM1 (as in the Boolean function of FIG. 6C) could therefore result from oxidative stress. On the other hand, NCF4, also known as P40PHOX, is known to downregulate, under some conditions, the NADPH-oxidase, a phagocyte enzyme system that creates a superoxide-producing "oxidative burst" in response to invasive microorganisms. In this case, local oxidative stress would result from the reduced levels of P40PHOX activity.

Taken together, the above observations resulting from the techniques disclosed herein are useful to researchers and are consistent with the Boolean function of FIG. 6C. The absence of NCF4, if accompanied by other unknown factors, permits activation of the NADPH-oxidase, which could be aberrant, i.e., not necessarily responding to the presence of invasive microorganisms. If this happens, then the resulting oxidative burst, evidenced by PGM1 downregulation, is damaging to the cell, and is normally accompanied by triggering apoptotic mechanisms, which, however, are inhibited by the activated HGF resulting from the presence of hepsin. The damaged surviving cell may then become cancerous as a result of additional mutations.

Such an interpretation may be partially true or even not true at all. However, its credibility can be strengthened if a similar theme is encountered in other gene modules in accordance with the techniques disclosed herein. For example, as noted above, the same conditional entropy (0.1159) with the same Boolean function results if gene NCF4 is replaced with gene KRT6E (keratin 6E). It is known that mutations in keratin genes can prime cells to oxidative injury. In that case, KRG6E is absent due to its mutation, and the resulting oxidative injury is not stemming from NADPH-oxidation, but is still manifested by the absence of PGM1, and the apoptotic mechanisms are still inhibited by the presence of hepsin.

There are many more gene modules that are revealed by EMBP analysis in addition to those indicated in FIGS. 6A-6E. Any variety and number of gene modules can be used that have low entropy.

There are many more gene modules that can be revealed by EMBP analysis in addition to those indicated in FIGS. 6A-6E. The analysis can be repeated for various different values of the threshold parameter, which corresponds to different minimum microarray measurement levels that would be considered to be indicative of a gene being turned on. The results obtained for each threshold value describes a slightly different aspect of the underlying biological process leading to cancer. The sum of these results would then allow biologists to piece together elements of the biological pathway along with their interrelationships.

A notable feature of the EMBP method of the disclosed subject matter is that it can be systems-based, in the sense that it considers the synergistic contributions of sets of genes, rather than individual genes. As a result, the optimal gene module may not be a subset of the optimal gene module of size n−1, because the n members of the latter module may interact synergistically towards predicting disease in a manner that cannot be achieved if any one of the n members is removed.

The EMBP analysis of the disclosed subject matter provides an opportunity for fruitful cross-disciplinary collaboration, in which biologists use the "clues" resulting from the computational results to infer potential pathways, which they can validate with genetic experiments, as well as suggest further computational experiments. For example, if it is desired to identify which genes play synergistic roles with another particular gene in terms of causing disease, the presence of that gene can be "frozen" and the other genes in a module minimizing the entropy can be identified. Furthermore, the approach of the disclosed subject matter can immediately suggest to researchers novel potential therapeutic methods that would not be possible with traditional individual-gene approaches. For example, two genes that appear in the same Boolean function can be targeted by combining two already existing drugs targeting each of the genes.

The EMBP analysis of the disclosed subject matter is a significant new tool for medical researchers working synergistically with future efforts of diseased tissue genome sequencing. For example, a Boolean function such as a'bc would suggest to a researcher the possibility that gene a may be inactivated due to its mutation or to hypermethylation of its promoter, as previously discussed regarding KRT6E and GSTP1, respectively. This observation may provide motivation to the researcher to sequence gene a in diseased tissues.

When EMBP analysis is attempted in datasets in which one of the two classification tissues had about 20 samples, there may be a finding of zero entropy with only one or two genes, which would be not provide new information compared to the individual gene ranking traditional approaches. However, if several hundred tissues are used in each classification set, then the gene modules, in accordance with the present subject matter, will contain a large number of genes, and the resulting Boolean functions, derived after running on high-end processors (including Boolean parsimony with heuristic methods), will accurately provide clues to researchers for inferring pathways.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope of the disclosed subject matter.

What is claimed is:

1. A method for predicting the presence of a disease in a subject by selecting factors from a data set of measurements, the measurements including values of the factors and outcomes, comprising:
    identifying two or more factors that are jointly associated with one or more outcomes from the data set, wherein the two or more factors comprise two or more genes, the data includes gene expression data comprising expression levels for each of the two or more genes, and the one or more outcomes includes presence or absence of the disease;
    analyzing each of the two or more factors to determine at least one interaction among the factors with respect to an outcome;
    identifying the interactions that connect the expression levels in the two or more factors with presence or absence of the disease; and
    predicting the presence of the disease in the subject by assessing the presence or absence of the interactions correlated with presence of the disease in the subject.

2. The method of claim 1, wherein the two or more factors comprise a module of factors.

3. The method of claim 2, wherein the at least one interaction comprises a structure of interactions.

4. The method of claim 2, wherein the at least one interaction comprises a logic function.

5. The method of claim 4, wherein the two or more genes comprise a module of genes.

6. The method of claim 5, wherein the module of genes comprise a smallest module of genes with joint expression levels that can be used for the prediction of the presence of the disease in the subject with high accuracy.

7. The method of claim 6, wherein the logic function comprises a simplest logic function connecting the genes to achieve the prediction.

8. A method for predicting the presence of a disease in a subject by selecting two or more genes from gene expression data, the gene expression data including expression levels for each of the two or more genes, comprising:
    providing gene expression data for two or more genes, the gene expression data comprising expression levels for each of the two or more genes;
    discretizing the gene expression data;
    identifying the two or more genes with a minimal conditional entropy; and
    identifying an interaction that connects the expression levels in the two or more genes with presence or absence of the disease; and
    predicting the presence of the disease in the subject by assessing the presence or absence of the interaction correlated with presence of the disease in the subject.

9. The method of claim 8, wherein the gene expression data is derived from at least one microarray of gene expression data.

10. The method of claim 8, wherein the two or more genes comprise a module of genes.

11. The method of claim 8, wherein the interaction is modeled using a most parsimonious Boolean function.

12. A system for predicting the presence of a disease in a subject by selecting two or more genes from gene expression data, the gene expression data including expression levels for each of the two or more genes, comprising:
    at least one processor, and
    a computer readable medium coupled to the at least one processor, having stored thereon instructions which when executed cause the processor to:
    provide gene expression data for the two or more genes, the gene expression data includes expression levels for each of the two or more genes;
    discretize the gene expression data;
    choose a single threshold for each of the two or more genes;
    identify the two or more genes with a minimal conditional entropy; and
    identify an interaction that connects the expression levels in the two or more genes with presence of the disease; and
    predict the presence of the disease in the subject by assessing the presence or absence of the interaction correlated with presence of the disease in the subject.

13. The system of claim 12, wherein the gene expression data is derived from a microarray of gene expression data.

14. The system of claim 12, wherein the two or more genes comprise a module of genes.

15. The system of claim 12, wherein the interaction comprises a most parsimonious Boolean function.

16. A system for predicting the presence of a disease in a subject by selecting factors from a data set of measurements, each measurement comprising values of the factors and outcomes, comprising:

at least one processor, and a computer readable medium coupled to the at least one processor, having stored thereon instructions which when executed cause the at least one processor to:

identify two or more factors that are jointly associated with one or more outcomes from the data, wherein the two or more factors comprise two or more genes, the data comprises gene expression data comprising expression levels for each of the two or more genes, and the one or more outcomes comprise presence or absence of the disease; and analyze each of the two or more factors to determine at least one interaction among the factors with respect to an outcome;

identifying the interactions that connect the expression levels in the two or more factors with presence or absence of the disease; and predicting the presence of the disease in the subject by assessing the presence or absence of the interactions correlated with presence of the disease in the subject.

17. The system of claim 16, wherein the two or more factors comprise a module of factors.

18. The system of claim 17, wherein the at least one interaction comprises a structure of interactions.

19. The system of claim 17, wherein the at least one interaction comprises a logic function.

20. The system of claim 16, wherein the two or more genes comprise a module of genes.

21. The system of claim 20, wherein the module of genes comprises a smallest module of genes with joint expression levels that can be used for a prediction of the presence of disease with high accuracy.

22. The system of claim 21, wherein the logic function comprises the simplest logic function connecting the genes to achieve the prediction.

* * * * *